US010954267B2

(12) United States Patent
Christensen et al.

(10) Patent No.: US 10,954,267 B2
(45) Date of Patent: Mar. 23, 2021

(54) DIPEPTIDE COMPRISING A NON-PROTEOGENIC AMINO ACID

(71) Applicant: Novo Nordisk A/S, Bagsvaerd (DK)

(72) Inventors: Caspar Christensen, Broenshoej (DK); Michael Raunkjaer, Vaerloese (DK); Rune Severinsen, Roskilde (DK); Jens C. Norrild, Birkeroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 16/028,065

(22) Filed: Jul. 5, 2018

(65) Prior Publication Data

US 2019/0002496 A1 Jan. 3, 2019

Related U.S. Application Data

(63) Continuation of application No. 15/383,598, filed on Dec. 19, 2016, now abandoned, which is a continuation of application No. 14/368,465, filed as application No. PCT/EP2012/076408 on Dec. 20, 2012, now abandoned.

(60) Provisional application No. 61/593,524, filed on Feb. 1, 2012.

(30) Foreign Application Priority Data

Dec. 29, 2011 (EP) .................... 11195998

(51) Int. Cl.
| C07K 5/06 | (2006.01) |
| C07K 5/078 | (2006.01) |
| C07K 14/605 | (2006.01) |
| C07K 1/107 | (2006.01) |
| C07K 4/00 | (2006.01) |
| C07K 14/00 | (2006.01) |

(52) U.S. Cl.
CPC .......... *C07K 5/06147* (2013.01); *C07K 1/107* (2013.01); *C07K 4/00* (2013.01); *C07K 5/06* (2013.01); *C07K 14/001* (2013.01); *C07K 14/605* (2013.01)

(58) Field of Classification Search
None
See application file for complete search history.

(56) References Cited

U.S. PATENT DOCUMENTS

| 6,277,819 B1 | 8/2001 | Efendic |
| 2001/0011071 A1 | 8/2001 | Knudsen et al. |
| 2003/0144471 A1 | 7/2003 | Jonassen et al. |
| 2008/0004429 A1 | 1/2008 | Roberts et al. |
| 2010/0317057 A1 | 12/2010 | Lau et al. |

FOREIGN PATENT DOCUMENTS

| EP | 733644 A1 | 9/1996 |
| EP | 869135 A1 | 10/1998 |
| WO | 9808871 A1 | 3/1998 |
| WO | 2005/027978 A2 | 3/2005 |
| WO | 2005/058958 A2 | 6/2005 |
| WO | 2006/005667 A2 | 1/2006 |
| WO | 2006/037810 | 4/2006 |
| WO | 2006/097536 A2 | 9/2006 |
| WO | 2006/097537 A2 | 9/2006 |
| WO | 2006/097538 | 9/2006 |
| WO | 2007147816 A1 | 12/2007 |
| WO | 2009/083549 A1 | 7/2009 |
| WO | 2010125079 A2 | 11/2010 |

OTHER PUBLICATIONS

Bourgault S et al "Novel stable PACAP 1,2 analogs with potent activity towards the PAC1 receptor",Journal: Peptides, Elsevier, Amsterdam,vol. 29, No. 6, Year Jun. 1, 2008,pp. 919-932, XP022646976,ISSN: 0196-9781.
Hodgson D R W et al., Chemical Reviews, "The Synthesis of Peptides and Proteins Containing Non-Natural Amino Acids", 2004, vol. 33, No. 7, pp. 422-430.
Makino Tomohiro et al., Biopolymers, "Semisynthesis of Human Ghrelin: Condensation of a Boc-Protected Recombinant Peptide With a Synthetic O-Acylated Fragment", 2005, vol. 79, No. 5, pp. 238-247.
Okada Y, Current Organic Chemistry, "Synthesis of Peptides by Solution Methods", 2001, vol. 5, No. 1, pp. 15707.
Wallace C J A, Current Opinion in Biotechnology, "Peptide Ligation and Semisynthesis", 1995, vol. 6, No. 4, pp. 403-410.
Gabor et al. "The first semi-synthetic serine protease made by native chemical ligation." Protein Expression and Purification. 2003. vol. 29. pp. 185-192.

*Primary Examiner* — Thomas S Heard
(74) *Attorney, Agent, or Firm* — Leon Y. Lum

(57) ABSTRACT

Described is a dipeptide comprising a non-proteogenic amino acid, methods of making such and methods of using said dipeptide in a process of making a polypeptide or protein comprising one or more non-proteogenic amino acids.

18 Claims, No Drawings

DIPEPTIDE COMPRISING A NON-PROTEOGENIC AMINO ACID

CROSS-REFERENCE TO RELATED APPLICATIONS

This application is a continuation of U.S. application Ser. No. 15/383,598, filed Dec. 19, 2016, which is a continuation of U.S. application Ser. No. 14/368,465, filed Jun. 24, 2014, which is a 35 U.S.C. § 371 National Stage application of International Application PCT/EP2012/076408 (WO 2013/098191), filed Dec. 20, 2012, which claims priority to European Patent Application 11195998.7, filed Dec. 29, 2011; this application claims priority under 35 U.S.C. § 119 to U.S. Provisional Application 61/593,524, filed Feb. 1, 2012; the contents of which are incorporated herein by reference.

TECHNICAL FIELD

The present invention is related to a dipeptide comprising a non-proteogenic amino acid, methods of making such and methods of using said dipeptide for producing a polypeptide or protein comprising one or more non-proteogenic amino acids.

BACKGROUND

A large number of polypeptides and proteins have been approved for use in medical practice. The polypeptides and proteins may be produced in suitable host cells by recombinant DNA technology or they may be produced synthetically by well-established peptide synthesis technology. However, native polypeptides and proteins tend to exhibit high clearance rates which are unacceptable for many clinical indications where a high plasma concentration of the polypeptide is required over a prolonged period of time.

The native polypeptides and proteins may be altered from the natural form to analogues and derivatives thereof to change or enhance certain characteristics. For example non-proteogenic amino acids (i.e. non-natural amino acids) may be added or substituted into polypeptides or proteins to e.g. confer a certain protection against hydrolysis (such as hydrolysis by DPP-IV of GLP-1 peptides).

Polypeptides containing one or more non-proteogenic amino acids such as N-terminally modified GLP-1 analogues may be prepared by introducing the non-proteogenic amino acid(s) via chemical synthesis in a stepwise manner wherein a coupling step followed by a deprotection step is applied for each amino acid to be added to the polypeptide or protein.

The stepwise synthesis is however time-consuming and inconvenient, it may lead to the formation of many byproducts, intermediate purification steps may be needed, and it may result in a significant amount of racemisation of some amino acid residues such as histidine residues.

Alternatively a peptide fragment including the non-proteogenic amino acid(s) may be coupled to the remaining polypeptide or protein where the fully protected fragment, such as e.g. a fragment protected on the N-terminal amino group and the side chain amino groups, is used in the method.

Such peptide fragment may, however, not be soluble in aqueous media limiting its use. Moreover, several deprotection steps are needed if orthogonal protecting groups are present in the fragment and if isolated, intermediate purifi-cations may be necessary between synthetic steps, and problems of intermediate isolation may occur.

WO 2009/083549 is related to a method for the preparation of GLP-1 analogues and derivatives containing non-proteogenic amino acids. Patent applications WO 2007/147816 A1 and WO 2010/125079 A2 are related to synthetic coupling of peptide fragments. Bourgault, S. et al. describe in PEPTIDES, vol. 29, no. 6(1), June 2008, pages 919-932 the use of conventional peptide chemistry.

A peptide fragment for use in an improved method for obtaining polypeptides containing one or more non-proteogenic amino acids is still needed.

SUMMARY

The present invention is related to a dipeptide of Chem. 1:

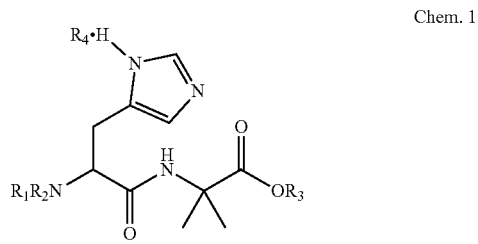

Chem. 1 wherein

R1 is H or an amino protecting group, and R2 is an amino protecting group; or

R1 is a removable alkyl group, and R2 is H or a removable alkyl group; or

R1 and R2 are jointly forming a ring;

R3 is H, or a secondary ammonium cation, a tertiary ammonium cation or a metal cation forming a salt with the carboxylate group; and R4 is absent or an acidic salt.

Also contemplated is a method for producing a dipeptide of the invention.

Furthermore, a method for obtaining a polypeptide or protein comprising one or more non-proteogenic amino acids is described, wherein the method comprises a step of reacting a dipeptide of the invention with a polypeptide or protein.

The invention may also solve further problems that will be apparent from the disclosure of the exemplary embodiments.

DESCRIPTION

The present invention is related to a dipeptide comprising a non-proteogenic amino acid, wherein the dipeptide is suitable for coupling to a polypeptide or protein.

In one aspect, the dipeptide of the invention has a free unprotected imidazolyl moiety. In one aspect, the dipeptide of the invention is in the form of a carboxylic acid salt.

In one aspect of the invention, the dipeptide is of Chem. 1:

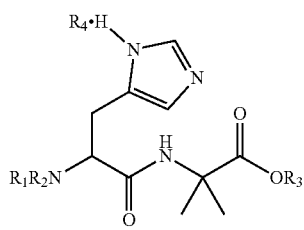

Chem. 1 wherein

R1 is H or an amino protecting group such as, but not limited to, Boc, Trt, Bpoc, Fmoc, Nsc, Cbz, Alloc, oNBS, pNBS, dNBS, ivDde or Nps, and R2 is an amino protecting group such as, but not limited to, Boc, Trt, Bpoc, Fmoc, Nsc, Cbz, Alloc, oNBS, pNBS, dNBS, ivDde or Nps; or R1 is a removable alkyl group such as, but not limited to benzyl or tert-Butyl, and R2 is H or a removable alkyl group such as, but not limited to, benzyl or tert-Butyl; or R1 and R2 are jointly forming a ring such as, but not limited to, phatalimide or 1,3,5-dioxazine;

R3 is H, or a secondary ammonium cation, a tertiary ammonium cation or a metal cation, such as an alkali metal cation or an alkaline earth metal cation, forming a salt with the carboxylate group; and R4 is absent or an acidic salt such as but not limited to a salt of TFA, HCl, HBr or hydrogensulfate.

In one aspect of the invention, R1 is H and R2 is an amino protecting group such as, but not limited to, Boc, Trt, Bpoc, Fmoc, Nsc, Cbz, Alloc, oNBS, pNBS, dNBS, ivDde or Nps; or R1 and R2 are jointly forming a ring such as, but not limited to, phatalimide or 1,3,5-dioxazine; or R1 is a removable alkyl group such as, but not limited to benzyl or tert-Butyl and R2 is H or a removable alkyl group such as, but not limited to benzyl or tert-Butyl.

In one aspect, R1 is H and R2 is a base sensitive protecting group such as, but not limited to, Fmoc. In one aspect, R1 is H and R2 is Fmoc.

When used herein, the term "amino protecting group" is to be understood as a protecting group (alternative term: protective group) known to the person skilled in the art of peptide chemistry which is introduced into the dipeptide by chemical modification of an amine (functional) group in order to prevent reaction on the very same amine during a chemical reaction.

When used herein, the term "removable alkyl group" is to be understood as an alkyl group, such as but not limited to a benzyl group, which can be removed by catalytical hydrogenolysis methodology. In one aspect of the invention R1 is benzyl and R2 is H.

R3 may be hydrogen, a secondary ammonium cation, a tertiary ammonium cation or a metal cation, wherein the secondary ammonium cation, the tertiary ammonium cation or the metal cation forms a salt with the carboxylate group to which it is adjacent. In one aspect of the invention the metal cation is an alkali metal cation or an alkaline earth metal cation. In one aspect R3 is selected from the group consisting of: H, lithium cation, sodium cation, potassium cation, caesium cation, calcium cation, magnesium cation, a cation derived from a secondary amine such as but not limited to N,N-dicyclohexyl ammonium cation, N,N-ditert-butyl amonium cation or a cation derived from a tertiary amine such as but not limited to triethylammonium cation.

In one aspect of the invention R3 is H. In one aspect R3 together with the carboxylate group to which it is adjacent forms a salt, such as but not limited to, a monovalent salt, a bivalent salt, or a salt derived from an amine.

According to an aspect of the invention R3 may be a secondary ammonium cation, a tertiary ammonium cation or a metal cation, such as an alkali metal cation or an alkaline earth metal cation, forming a salt with the carboxylate group to which it is adjacent. The salt between R3 and the carboxylate group may e.g. be a monovalent salt, such as but not limited to an alkali salt including a lithium salt, a sodium salt, a potassium salt or a caesium salt, a bivalent salt such as but not limited to a calcium salt or a magnesium salt, a salt derived from a secondary amine such as, but not limited to, N,N-dicyclohexylamine or N,N-ditert-butylamine or a salt derived from a tertiary amine such as, but not limited to, triethylamine.

It has surprisingly been found by the inventors that the dipeptide of the invention where R3 is H, or is a secondary ammonium cation, a tertiary ammonium cation or a metal cation which forms a salt with the carboxylate group to which it is adjacent, and R4 is absent or an acidic salt is particularly good in e.g. an aqueous acylation reaction where the dipeptide is reacted with a peptide or polypeptide.

In one aspect of the invention, R4 is absent. In one aspect, R4 is an acidic component forming a salt with the dipeptide. In one aspect, R4 is selected from the group consisting of: TFA, HCl, HBr and hydrogensulfate. In one aspect R4 is TFA.

In one aspect, the dipeptide of the invention is the enantiomeric or racemic dipeptide Fmoc-His-Aib-OH of Chem. 2

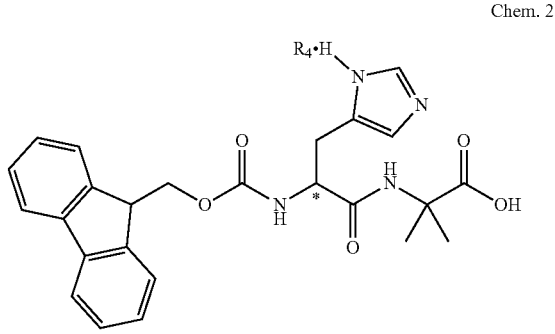

Chem. 2 wherein * indicates the chiral center of the dipeptide and R4 is absent or an acidic component such as, but not limited to, TFA, HCl, HBr or hydrogensulfate, said acidic component forming a salt with the dipeptide. In one aspect R4 is TFA.

Herein the term "enantiomeric" in a sample of compounds, is to be understood as an excess of one enantiomeric form, i.e. either the L- or the D-form, in the sample. When used herein, the term "racemic" is to be understood as equivalent amounts of L- and D-form in a sample of compounds. As a non-limiting example, the histidine residue of the enantiomeric Fmoc-His-Aib-OH of Chem. 2 may be in the form of L-histidine or D-histidine.

In one aspect of the invention, the dipeptide of Chem. 1 or Chem. 2 is activated by an activating agent known by a person skilled in the art. In one aspect, the dipeptide of Chem. 1 or Chem. 2 is activated by a phosphonium based coupling reagent. In one aspect, the phosphonium based coupling reagent is selected from the group consisting of:

Benzotriazol-1-yl-oxy-tris-(dimethylamino)-phosphonium hexafluorphosphate (BOP), (Benzotriazol-1-yloxy)tripyrrolidinophosphonium hexafluorophosphate (PyBOP), (7-Azabenzotriazol-1-yloxy) tripyrrolidinophosphonium hexafluorophosphate (PyAOP), 6-Chloro-benzotriazole-1-yl-oxy-tris-pyrrolidinophosphonium hexafluorophosphate (PyClocK), O-[(1-cyano-2-ethoxy-2-oxoethylidene)amino]-oxytri(pyrrolidin-1-yl) phosphonium hexafluorophosphate PyOxP, O-[(1-cyano-2-ethoxy-2-oxoethylidene)amino]-oxytri(pyrrolidin-1-yl) phosphonium tetrafluoroborate (PyOxB). In one aspect phosphonium based coupling reagent is Benzotriazol-1-yloxy)tripyrrolidinophosphonium hexafluorophosphate (PyBOP).

The term "phosphonium based coupling reagent" is herein to be understood as a coupling reagent containing a phosphonium salt which, when reacting in situ with a carboxylic acid, forms an activated carboxylic acid to be reacted with a polypeptide or protein.

The dipeptide of the invention is surprisingly stable and has a long shelf-life.

When used herein the term "stabilized" or "stable" when referring to a dipeptide of the invention refers to a dipeptide with increased chemical stability, increased physical stability or increased physical and chemical stability.

In one aspect a dipeptide of the invention is stable for more than 6 weeks of usage and for more than 2 years of storage. In another aspect a dipeptide of the invention is stable for more than 4 weeks of usage and for more than two years of storage. In a further aspect a dipeptide of the invention is stable for more than 4 weeks of usage and for more than 3 years of storage. In an even further aspect a dipeptide of the invention is stable for more than 2 weeks of usage and for more than 1 year of storage.

When used herein the term "ambient temperature" means the temperature of the surroundings. Under indoors conditions, ambient temperature is the same as room temperature and may e.g. be 25° C.

The dipeptide of the invention is easy to handle and the use thereof in peptide chemistry is easy compared to conventional step by step solid phase peptide synthesis due to reduced amount of chemical modification steps, such as deprotection and activation steps.

According to an aspect, the dipeptide of the invention may be used in a method for obtaining a polypeptide or protein comprising one or more non-proteogenic amino acids.

In one aspect, the dipeptide according to the invention is used in a process for coupling covalently the dipeptide to a polypeptide or protein. In one aspect, the dipeptide is used in a process for coupling the dipeptide to the N-terminal amine of a polypeptide or protein. In one aspect, the dipeptide is used in a process for coupling the dipeptide to nucleophiles in other molecules not belonging to the chemical group of polypeptides and/or proteins.

In one aspect, the polypeptide or protein to which the dipeptide is coupled consists of proteogenic amino acids, i.e. the polypeptide or protein to which the dipeptide is coupled does not comprise any non-proteogenic amino acids.

In one aspect of the invention, the dipeptide of Chem. 1 or Chem. 2 is used for coupling said dipeptide to a polypeptide or protein to form an amide bond between the carboxylate group of the dipeptide of Chem. 1, i.e. the functional group containing R3, or the carboxylic acid of Chem. 2 and a free amine of a polypeptide or protein. In one aspect, the dipeptide of Chem. 1 or Chem. 2 is reacted to a polypeptide or protein in an aqueous media to form an amide bond between the carboxylic acid of the dipeptide of Chem. 1 or Chem. 2 and the N-terminal amine of a polypeptide or protein.

According to an aspect of the invention, R1 and/or R2 is removed after completion of the reaction with a polypeptide or protein. In one aspect, R1 and/or R2 is removed in one chemical step. In one aspect, R1 and/or R2 is removed in a deprotection step under basic conditions. In one aspect, R1 and/or R2 is removed in a deprotection step comprising adding base to the reaction medium. In one aspect, R1 and/or R2 is removed in a deprotection step comprising adding an amine to the reaction medium. In one aspect, R1 and/or R2 is removed in a deprotection step comprising adding piperidine to the reaction medium.

In one aspect of the invention, R1 and/or R2 is removed in situ in one chemical step after completion of the acylation reaction with a polypeptide or protein.

According to one aspect, the dipeptide of the invention may be used in a method for obtaining a polypeptide or protein comprising one or more non-proteogenic amino acids. In one aspect, the reaction is carried out in solution. In one aspect, the activated dipeptide of the invention is reacted with a polypeptide or protein dissolved in an aqueous media. In one aspect, the coupling reaction is carried out in a solid phase peptide synthesis as known by the person skilled in the art. It has by the inventors been found that by using said method for obtaining a polypeptide or protein comprising one or more non-proteogenic amino acids and a histidine N-terminally thereto, a polypeptide or protein product is obtained in which the histidine residue is not or only slightly racemized.

In one aspect the method for obtaining a polypeptide or protein comprising one or more non-proteogenic amino acids comprises the following steps:
1. activating the dipeptide with a phosphonium based coupling reagent
2. reacting the activated dipeptide with a polypeptide or protein
3. removing the protecting group(s) in situ whereby the final polypeptide or protein is obtained.

In one aspect the method for obtaining a polypeptide or protein comprising one or more non-proteogenic amino acids comprises the following steps:
1. activating the dipeptide of chem. 1 or chem. 2 with a phosphonium based coupling reagent
2. reacting the activated dipeptide with a polypeptide or protein
3. removing the protecting group(s) in situ whereby the final polypeptide or protein is obtained.

In one aspect, the activated dipeptide is reacted with a polypeptide or protein in an aqueous media. As used herein the terms "aqueous medium" or "aqueous media" include any water based medium, e.g., water, saline solution, a sugar solution, a transfusion solution, a buffer, and any other readily available water-based medium. Further, an aqueous media may contain one or more water soluble organic solvents such as, but not limited to, dimethylformamide (DMF), N-methyl-2-pyrrolidone (NMP), dimethylacetamide (DMAC), dimethyl sulfoxide (DMSO), acetonitrile, dioxane, a water soluble acetal such as e.g. dimethyl acetal, diethyl acetal or 1,3-dioxalane and a water soluble alcohol such as e.g. methanol, ethanol, propanol, 2-propanol and butoxy-2-ethanol.

In one aspect, the aqueous media in which the activated dipeptide is reacted with a polypeptide or protein comprises 100-10% water and thus 0-90% further solvent(s), where non-limiting examples of further solvents e.g. may be selected from the group consisting of DMF, NMP, DMAC, DMSO, acetonitrile, dioxane, a water soluble acetal such as e.g. dimethyl acetal, diethyl acetal or 1,3-dioxalane and a water soluble alcohol such as e.g. methanol, ethanol, propanol, 2-propanol and butoxy-2-ethanol. In one aspect the aqueous media comprises 80-20% water, such as 60-30% water. In one aspect the aqueous media comprises 50-30% water. In one aspect the aqueous media comprises about 50% water. In one aspect the aqueous media comprises about 40% water. In one aspect the aqueous media comprises about 30% water.

In one aspect of the invention the dipeptide is dissolved in an aprotic organic solvent or a mixture thereof such as, but not limited to, DMF, NMP, DMAC, DMSO, acetonitrile and dioxane, before it is added to the aqueous media wherein it is reacted with a peptide or polypeptide.

When used herein the term "aprotic" is used for solvents such as e.g. acetone or dichloromethane which tend to have large dipole moments, i.e. separation of partial positive and partial negative charges within the same molecule, and solvate positively charged species via their negative dipole. Examples of aprotic solvents include, but is not limited to, dichloromethane (DCM), tetrahydrofuran (THF), ethyl acetate, acetone, DMF, NMP, DMAC, DMSO, acetonitrile, dioxane and propylene carbonate.

In one aspect, the activated dipeptide is reacted with a polypeptide or protein on solid phase using a procedure known by the person skilled in the art of peptide chemistry, as e.g. described in ISBN 0-7167-7009-1 "Synthetic Peptides", ed. Gregory A. Grant.

In one aspect the phosphonium based coupling reagent is PyBOP. In one aspect the protecting group is Fmoc. In one aspect the final polypeptide or protein is obtained in solution.

In one aspect the protecting group is removed under basic conditions. In one aspect the protecting group is removed at a pH which is at least 7. In one aspect the protecting group is removed by piperidine, DBU (1,8-diazabicyclooundec-7-ene) or tert-butylamine.

In one aspect of the invention, the pH of the aqueous reaction mixture in the acylation step is adjusted to between pH 7 and pH 14. In one aspect pH of the reaction medium is between pH 8 and pH 13. In another aspect the pH is between pH 8 and pH 12. In another aspect the pH is between pH 8 and pH 10. In another aspect the pH is between pH 8.3 and pH 9.7.

The "reaction mixture" is herein to be understood as the mixture of solvents and reagents used when reacting the dipeptide of the invention with a polypeptide or protein. The reaction mixture may be aqueous, i.e. water being present in the reaction mixture.

The pH of the reaction mixture may be controlled by means known to the person skilled in the art. For example a simple pH paper test (pH stick) or a pH-meter may be used to measure the pH and acid or base may be added manually to adjust the pH, or a pH-meter with a feed-back mechanism, which can control the pH of the solution, may be used.

Acids suitable for adjusting the pH include but are not limited to: Hydrochloric acid, sulphuric acid, hydrogen sulphate, phosphoric acid, citric acid and acetic acid.

Bases suitable for adjusting the pH include, but are not limited to: Tertiary amine bases such as, but not limited to, triethylamine or diisopropylethylamine, N-methylmorpholine, alkalimetal hydroxides such as, but not limited to, lithium hydroxide, sodium hydroxide, potassium hydroxide or cesium hydroxide and alkali carbonates such as, but not limited to, potassium carbonate, sodium carbonate, lithium carbonate, potassium hydrogen carbonate, sodium hydrogen carbonate or lithium hydrogen carbonate.

In one aspect of the invention the reaction mixture comprises a buffer. In one aspect of the invention the buffer is selected from the group consisting of: Phosphate buffer, Sodium carbonate buffer, Bicine N,N-Bis(2-hydroxyethyl)glycine buffer, HEPPS buffer (3-[4-(2-Hydroxyethyl)-1-piperazinyl]propanesulfonic acid buffer), HEPES buffer (4-(2-Hydroxyethyl)-1-piperazineethanesulfonic acid buffer), MOPS buffer (3-(N-Morpholino)propanesulfonic acid buffer) and TEA buffer (triethylamine buffer). In one aspect of the invention the reaction mixture comprises a TEA buffer (triethylamine buffer).

Before addition to the reaction mixture, the dipeptide may be activated, i.e. the carboxylic acid functionality of the dipeptide may be converted to an activated ester of said carboxylic acid. When activating the dipeptide of the invention, the temperature of the reaction mixture during the activation step may be between $-5°$ C. and $50°$ C. such as between $0°$ C. and $50°$ C. In one aspect the temperature is between $5°$ C. and $40°$ C. In another aspect the temperature is between $10°$ C. and $35°$ C. In a further aspect the temperature is between 15 and $25°$ C. In yet a further aspect the temperature is about $20°$ C. during the activation step.

The temperature of the reaction mixture during the acylation step, where the activated dipeptide of the invention is reacted with a polypeptide or protein, may be between $-5°$ C. and $50°$ C. such as between $0°$ C. and $50°$ C. In one aspect the temperature is between $5°$ C. and $40°$ C. In another aspect the temperature is between $10°$ C. and $35°$ C. In a further aspect the temperature is between 15 and $25°$ C. In yet a further aspect the temperature is about $20°$ C.

The term "polypeptide or protein" as used herein means a compound composed of at least two constituent amino acids connected by polypeptide bonds. The constituent amino acids may be chosen from the group of the amino acids encoded by the genetic code (proteogenic amino acids) and they may be natural amino acids which are not encoded by the genetic code, as well as synthetic amino acids (non-proteogenic amino acids). The 22 proteogenic amino acids are: Alanine, Arginine, Asparagine, Aspartic acid, Cysteine, Cystine, Glutamine, Glutamic acid, Glycine, Histidine, Hydroxyproline, Isoleucine, Leucine, Lysine, Methionine, Phenylalanine, Proline, Serine, Threonine, Tryptophan, Tyrosine and Valine.

Thus a non-proteogenic amino acid is a moiety which can be incorporated into a polypeptide or protein via polypeptide bonds but is not a proteogenic amino acid. Examples are γ-carboxyglutamate, ornithine, phosphoserine, the D-amino acids such as D-alanine and D-glutamine. Synthetic non-proteogenic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), ornithine, Dap (2,3-diaminopropionic acid), Dab (2,4-diaminobutanoic acid), Tle (tert-butylglycine), 3-aminomethyl benzoic acid, anthranilic acid, des-amino-Histidine, the beta analogs of amino acids such as β-alanine etc. D-histidine, desamino-histidine, 2-amino-histidine, β-hydroxy-histidine, homohistidine, $N^{α}$-acetyl-histidine, α-fluoromethyl-histidine, α-methyl-histidine, 3-pyridylalanine, 2-pyridylalanine or 4-pyridylalanine, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid or (1-aminocyclooctyl) carboxylic acid.

The term "analogue" as used herein referring to a polypeptide or protein means a modified polypeptide or protein wherein one or more amino acid residues of the polypeptide or protein have been substituted by other amino acid residues and/or wherein one or more amino acid residues have been deleted from the polypeptide or protein and/or wherein one or more amino acid residues have been deleted from the polypeptide or protein and or wherein one or more amino acid residues have been added to the polypeptide or protein. Such addition or deletion of amino acid residues can take place at the N-terminal of the polypeptide or protein and/or at the C-terminal of the polypeptide or protein. A simple system is often used to describe analogues: For example [Aib$^8$, Arg$^{34}$]GLP-1(7-37) designates a GLP-1(7-37) analogue wherein the naturally occurring alanine at position 8 is substituted with alpha-aminoisobutyric acid and lysine at position 34 has been substituted with arginine. All amino acids for which the optical isomer is not stated is to be understood to mean the L-isomer. In aspects of the invention a maximum of 17 amino acids have been modified. In aspects of the invention a maximum of 15 amino acids have been modified. In aspects of the invention a maximum of 10 amino acids have been modified. In aspects of the invention a maximum of 8 amino acids have been modified. In aspects of the invention a maximum of 7 amino acids have been modified. In aspects of the invention a maximum of 6 amino acids have been modified. In aspects of the invention a maximum of 5 amino acids have been modified. In aspects of the invention a maximum of 4 amino acids have been modified. In aspects of the invention a maximum of 3 amino acids have been modified. In aspects of the invention a maximum of 2 amino acids have been modified. In aspects of the invention 1 amino acid has been modified.

In one aspect of the invention, the C-terminal of the derivative according to the invention may be terminated as either an acid or amide. In one aspect, the C-terminal of the derivative of the invention is an amide. In another aspect, the C-terminal of the derivative of the invention is an acid.

The present invention is especially suitable for making polypeptides or proteins comprising one or more non-proteogenic amino acids suitable for treating e.g. diabetes such as glucagon-like peptides and insulins.

In one aspect the polypeptide or protein to be reacted with the dipeptide is a glucagon-like peptide.

The term "glucagon-like peptide" as used herein means the glucagon family of polypeptides, exendins and analogues thereof. The glucagon family of polypeptides are encoded by the preproglucagon gene and encompasses three small polypeptides with a high degree of homology, i.e. glucagon (1-29), GLP-1 (1-37) and GLP-2 (1-33). Exendins are polypeptides expressed in lizards and like GLP-1, are insulinotropic. Examples of exendins are exendin-3 and exendin-4.

The terms GLP-1, GLP-2, exendin-3 and exendin-4 are known to a person skilled in the art. For example "GLP-1 compound" or "GLP-1 polypeptide" as used herein means human GLP-1(7-37), insulinotropic analogue thereof and insulinotropic derivatives thereof. Non-limiting examples of GLP-1 analogues are GLP-1(7-36) amide, Arg$^{34}$-GLP-1(7-37), Aib$^8$Arg$^{34}$-GLP-1(7-37), Gly$^8$-GLP-1(7-37), Val$^8$-GLP-1(7-36)-amide and Val$^8$Asp$^{22}$-GLP-1(7-37). Non-limiting examples of GLP-1 derivatives are desamino-His$^7$, Arg$^{26}$, Lys$^{34}$(N$^\varepsilon$-γ-Glu (N$^\alpha$-hexadecanoyl)))-GLP-1(7-37), desamino-His$^7$, Arg$^{26}$, Lys$^{34}$(N$^\alpha$-octanolyl)-GLP-1(7-37), Arg$^{26,34}$, Lys$^{38}$(N$^\varepsilon$-(ω-carboxypentadecanoyl))-GLP-1(7-38), Arg$^{26,34}$, Lys$^{36}$(N$^\varepsilon$-(γ-Glu(N$^\alpha$-hexadecanoyl)))-GLP-1 (7-36) and Arg$^{34}$, Lys$^{26}$(N$^\varepsilon$-(γ-Glu(N$^\alpha$-hexadecanoyl)))-GLP-1(7-37). According to established practice in the art the GLP-1 nomenclature starts at the histidine residue which is referred to as no. 7, and subsequent amino acid residues are numbered accordingly, ending with glycine no. 37. Therefore, generally, any reference herein to an amino acid residue number or a position number of the GLP-1(7-37) sequence is to the sequence starting with His at position 7 and ending with Gly at position 37. GLP-1 analogues of the derivatives of the invention may be described by reference to i) the number of the amino acid residue in native GLP-1(7-37) which corresponds to the amino acid residue which is changed (i.e., the corresponding position in native GLP-1), and to ii) the actual change.

In one aspect the glucagon-like peptide according to the invention is dipeptidyl aminopeptidase IV protected. In another aspect the glucagon-like peptide according to the invention is dipeptidyl aminopeptidase IV protected.

The term "dipeptidyl aminopeptidase IV protected" as used herein means a glucagon-like peptide, e.g. a GLP-1 analogue, which is more resistant to dipeptidyl aminopeptidase IV (DPP-IV) than the native compound, e.g. GLP-1 (7-37). Such protection may be obtained by e.g. mutations and/or derivatization of the native compound. Resistance of a GLP-1 compound towards degradation by dipeptidyl aminopeptidase IV is determined by the following degradation assay:

Aliquots of the GLP-1 compound (5 nmol) are incubated at 37° C. with 1 μL of purified dipeptidyl aminopeptidase IV corresponding to an enzymatic activity of 5 mU for 10-180 minutes in 100 μL of 0.1 M triethylamine-HCl buffer, pH 7.4. Enzymatic reactions are terminated by the addition of 5 μL of 10% trifluoroacetic acid, and the polypeptide degradation products are separated and quantified using HPLC analysis. One method for performing this analysis is: The mixtures are applied onto a Vydac C18 widepore (30 nm pores, 5 μm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 1999; 79: 93-102 and Mentlein et al. Eur. J. Biochem. 1993; 214: 829-35. Polypeptides and their degradation products may be monitored by their absorbance at 220 nm (peptide bonds) or 280 nm (aromatic amino acids), and are quantified by integration of their peak areas related to those of standards. The rate of hydrolysis of a GLP-1 compound by dipeptidyl aminopeptidase IV is estimated at incubation times which result in less than 10% of the GLP-1 compound being hydrolysed.

The term "insulinotropic" as used herein referring to a glucagon-like peptide means the ability to stimulate secretion of insulin in response to an increased plasma glucose level. Insulinotropic glucagon-like peptides are agonists of the GLP-1 receptor. The insulinotropic property of a compound may be determined by in vitro or in vivo assays known in the art. The following in vitro assay may be used to determine the insulinotropic nature of a compound such as a glucagon-like peptide. Preferably insulinotropic compounds exhibit an EC$_{50}$ value in the below assay of less than 5 nM, even more preferably an EC$_{50}$ value of less than 500 μM.

Baby hamster kidney (BHK) cells expressing the cloned human GLP-1 receptor (BHK 467-12A) are grown in DMEM media with the addition of 100 IU/mL penicillin, 100 μL/mL streptomycin, 10% foetal calf serum and 1 mg/mL Geneticin G-418 (Life Technologies). Plasma membranes are prepared by homogenization in buffer (10 mM Tris-HCl, 30 mM NaCl and 1 mM dithiothreitol, pH 7.4, containing, in addition, 5 mg/mL leupeptin (Sigma), 5 mg/L pepstatin (Sigma), 100 mg/L bacitracin (Sigma), and 16 mg/L aprotinin (Calbiochem-Novabiochem, La Jolla, Calif.)). The homogenate is centrifuged on top of a layer of 41% W/v sucrose. The white band between the two layers is diluted in buffer and centrifuged. Plasma membranes are stored at −80° C. until used.

The functional receptor assay is carried out by measuring cAMP as a response to stimulation by the insulinotropic polypeptide or insulinotropic compound. Incubations are carried out in 96-well microtiter plates in a total volume of 140 mL and with the following final concentrations: 50 mM Tris-HCl, 1 mM EGTA, 1.5 mM $MgSO_4$, 1.7 mM ATP, 20 mM GTP, 2 mM 3-isobutyl-1-methylxanthine (IBMX), 0.01% w/v Tween-20, pH 7.4. Compounds are dissolved and diluted in buffer. GTP is freshly prepared for each experiment: 2.5 µg of membrane is added to each well and the mixture is incubated for 90 min at room temperature in the dark with shaking. The reaction is stopped by the addition of 25 mL 0.5 M HCl. Formed cAMP is measured by a scintillation proximity assay (RPA 542, Amersham, UK). A dose-response curve is plotted for the compound and the $EC_{50}$ value is calculated using GraphPad Prism software.

The term "prodrug of an insulinotropic compound" as used herein means a chemically modified compound which following administration to the patient is converted to an insulinotropic compound. Such prodrugs are typically amino acid extended versions or esters of an insulinotropic compound.

The term "exendin-4 compound" as used herein is defined as exendin-4(1-39), insulinotropic fragments thereof, insulinotropic analogs thereof and insulinotropic derivatives thereof. Insulinotropic fragments of exendin-4 are insulinotropic polypeptides for which the entire sequence can be found in the sequence of exendin-4 and where at least one terminal amino acid has been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogs of exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. An example of an insulinotropic analog of exendin-4(1-39) is $Ser^2Asp^3$-exendin-4(1-39) wherein the amino acid residues in position 2 and 3 have been replaced with serine and aspartic acid, respectively (this particular analog also being known in the art as exendin-3). Insulinotropic derivatives of exendin-4(1-39) and analogs thereof are what the person skilled in the art considers to be derivatives of these polypeptides, i.e. having at least one substituent which is not present in the parent polypeptide molecule with the proviso that said derivative either is insulinotropic or is a prodrug of an insulinotropic compound. Examples of substituents are amides, carbohydrates, alkyl groups, esters and lipophilic substituents. An example of an insulinotropic derivative of exendin-4(1-39) and analog thereof is $Tyr^{31}$-exendin-4(1-31)-amide.

The term "stable exendin-4 compound" as used herein means a chemically modified exendin-4(1-39), i.e. an analogue or a derivative which exhibits an in vivo plasma elimination half-life of at least 10 hours in man, as determined by conventional methods.

The term "dipeptidyl aminopeptidase IV protected exendin-4 compound" as used herein means an exendin-4 compound which is more resistant towards the plasma peptidase dipeptidyl aminopeptidase IV (DPP-IV) than exendin-4, as determined by the assay described under the definition of dipeptidyl aminopeptidase IV protected GLP-1 compound.

The GLP-1 analogues may be such wherein the naturally occurring Lys at position 34 of GLP-1(7-37) has been substituted with Arg.

Also, derivatives of precursors or intermediates of insulinotropic polypeptides are covered by the invention.

In one aspect of the invention the glucagon-like peptide is insulintropic. In a further aspect the insulintropic glucagon-like peptide is selected from the group consisting of GLP-1, GLP-2, exendin-4, exendin-3 and analogues and derivatives thereof.

Conformational stability of protein based drugs is important for maintaining biological activity and for minimizing irreversible loss of structure due to denaturation and fibrillation. Especially large insulinotropic polypeptides and proteins are labile with respect to conformational change due to complicated refolding patterns. Also, insulinotropic polypeptides with a known history of fibrillation, such as GLP-1, are particularly sensitive towards destabilization of tertiary structure (i.e. formation of a molten globular state).

In one aspect, the constituent amino acids of a glucagon-like peptide according to the invention may be selected from the group of the amino acids encoded by the genetic code and they may be natural amino acids which are not encoded by the genetic code, as well as synthetic amino acids. Natural amino acids which are not encoded by the genetic code are e.g. hydroxyproline, γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), β-alanine, 3-aminomethyl benzoic acid, anthranilic acid.

In one aspect of the invention, the glucagon-like peptide to be reacted with the dipeptide according to the invention is a GLP-1 polypeptide. In a further aspect the GLP-1 polypeptide is a GLP-1 peptide having a side chain mentioned in WO 2006/005667, WO 2005/027978, WO 2011/080103 or WO 2006/097537. In one aspect the GLP-1 polypeptide is GLP-1(9-37); $Arg^{34}$-GLP-1(9-37); $Aib^{22}$, $Arg^{34}$-GLP-1(9-37); $Arg^{34}$, $Pro^{37}$-GLP-1(9-37) or $Aib^{22,27,30,35}$, $Arg^{34}$, $Pro^{37}$-GLP-1 (9-37)amide having a side chain mentioned in WO 2006/005667, WO 2005/027978, WO 2011/080103 or WO 2006/097537. In one aspect the GLP-1 polypeptide is a GLP-1 peptide mentioned in WO 2011/080103 page 84, line 24 to page 95, line 2, or a GLP-1 analogue mentioned in WO 2006/097537 page 19, line 25 to page 22, line 4.

In another aspect the glucagon-like peptide to be reacted with the dipeptide according to the invention is a GLP-1 polypeptide which is selected from the group consisting of:

$Arg^{34}$-GLP-1(9-37);
$Aib^{22}$, $Arg^{34}$-GLP-1(9-37);
$Arg^{34}$, $Pro^{37}$-GLP-1(9-37);
$Aib^{22,27,30,35}$, $Arg^{34}$, $Pro^{37}$-GLP-1 (9-37)amide;
$N^{\varepsilon 26}$-[2-(2-{2-[10-(4-Carboxyphenoxy)decanoylamino] ethoxy} ethoxy)acetyl], $N^{\varepsilon 37}$-[2-(2-{2-[10-(4-Carboxyphenoxy)decanoylamino]ethoxy}ethoxy)acetyl]-[$Arg^{34}$, $Lys^{37}$]-GLP-1(9-37)-peptide;

N$^{ε26}${2-[2-(2-{2-[2-(2-{(S)-4-Carboxy-4-[10-(4-carboxy-phenoxy)decanoylamino]butyrylamino}-ethoxy)ethoxy]acetylamino}ethoxy)ethoxy]acetyl}, N$^{ε37}$-{2-[2-(2-{2-[2-(2-{(S)-4-carboxy-4-[10-(4-carboxyphenoxy)decanoylamino]butyrylamino}ethoxy)ethoxy]acetylamino}-ethoxy)ethoxy]acetyl}-[Arg$^{34}$, Lys$^{37}$]GLP-1)(9-37)-peptide;

N$^{ε26}$-[2-(2-{2-[2-(2-{2-[(S)-4-Carboxy-4(15-carboxypentadecanoylamino)butyrylamino]-ethoxy}ethoxy)acetylamino]ethoxy}ethoxy)acetyl], N$^{ε37}$-[2-(2-{2-[2-(2-{2-[(S)-4-Carboxy-4-(15-carboxypentadecanoylamino)butyrylamino]ethoxy}ethoxy)acetylamino]ethoxy}-ethoxy) acetyl][Arg$^{34}$, Lys$^{37}$]GLP-1(9-37)-peptide amide;

N$^{ε26}$-[2-(2-{2-[2-(2{2-[(S)-4-Carboxy-4-(11-carboxyundecanoylamino)butyrylamino]ethoxy}-ethoxy) acetylamino]ethoxy}ethoxy)acetyl], N$^{ε37}$[2-(2-{2-[2-(2-{2[(S)-4-Carboxy-4-(11-carboxyundecanoylamino)butyrylamino]ethoxy}ethoxy)acetylamino]ethoxy}ethoxy)-acetyl][Arg$^{34}$, Lys$^{37}$]GLP-1(9-37)-peptide amide;

N$^{ε26}$-[2-[2-(2-{2-[(S)-4-Carboxy-4-(13-carboxytridecanoylamino)butyrylamino]ethoxy}ethoxy)-acetyl], N$^{ε37}$-[2-[2-(2-{2-[(S)-4-Carboxy-4-(13-carboxytridecanoylamino)butyrylamino]-ethoxy}ethoxy)acetyl][Arg$^{34}$, Lys$^{37}$]GLP-1(9-37)-peptide amide;

Nε$^{26}$ (17-carboxyheptadecanoyl)-[Arg34]GLP-1-(9-37)-peptide;

N$^{ε26}$-(19-carboxynonadecanoyl)-[Arg34]GLP-1-(9-37)-peptide;

N$^{ε26}$-[2-(2-[2-(2-[2-(2-[4-(17-Carboxyheptadecanoylamino)-4(S)-carboxybutyrylamino]-ethoxy)ethoxy]acetylamino)ethoxy]ethoxy)acetyl][Arg34]GLP-1-(9-37) peptide; and N$^{ε26}$-[2-(2-[2-(2-[2-(2-[4-(21-Carboxyuneicosanoylamino)-4(S)-carboxybutyrylamino]ethoxy)-ethoxy]acetylamino)ethoxy]ethoxy)acetyl][Arg34]GLP-1-(9-37)peptide.

In another aspect the glucagon-like peptide to be reacted with the dipeptide according to the invention is a GLP-1 polypeptide which is selected from the group consisting of:
Arg$^{34}$-GLP-1(9-37);
Aib$^{22}$, Arg$^{34}$-GLP-1(9-37);
Arg$^{34}$, Pro$^{37}$-GLP-1(9-37); and
Aib$^{22,27,30,35}$, Arg$^{34}$, Pro$^{37}$-GLP-1 (9-37)amide In another aspect the glucagon-like peptide to be reacted with the dipeptide according to the invention is a GLP-1 polypeptide which is selected from the group consisting of:
N$^{ε26}$-[2-(2-{2-[10-(4-Carboxyphenoxy)decanoylamino]ethoxy} ethoxy)acetyl], N$^{ε37}$-[2-(2-{2-[10-(4-Carboxyphenoxy)decanoylamino]ethoxy}ethoxy)acetyl][Arg$^{34}$, Lys$^{37}$]GLP-1(9-37)-peptide;

N$^{ε26}${2-[2-(2-{2-[2-(2-{(S)-4-Carboxy-4-[10-(4-carboxy-phenoxy)decanoylamino]butyrylamino}-ethoxy)ethoxy]acetylamino}ethoxy)ethoxy]acetyl}, N$^{ε37}$-{2-[2-(2-{2-[2-(2-{(S)-4-carboxy-4-[10-(4-carboxyphenoxy)decanoylamino]butyrylamino}ethoxy)ethoxy]acetylamino}-ethoxy)ethoxy]acetyl}-[Arg$^{34}$, Lys$^{37}$]GLP-1(9-37)-peptide;

N$^{ε26}$-[2-(2-{2-[2-(2-{2-[(S)-4-Carboxy-4-(15-carboxypentadecanoylamino)butyrylamino]-ethoxy}ethoxy)acetylamino]ethoxy}ethoxy)acetyl], N$^{ε37}$-[2-(2-{2-[2-(2-{2 [(S)-4-Carboxy-4-(15-carboxypentadecanoylamino)butyrylamino]ethoxy}ethoxy)acetylamino]ethoxy}-ethoxy)acetyl][Arg$^{34}$, Lys$^{37}$]GLP-1(9-37)-peptide amide;

N$^{ε26}$-[2-(2-{2-[2-(2-{2-[(S)-4-Carboxy-4-(11-carboxyundecanoylamino)butyrylamino]ethoxy}-ethoxy)acetylamino]ethoxy}ethoxy)acetyl], N$^{ε37}$-{2-[2-(2-{2-[2-(2-{[(S)-4-Carboxy-4-(11-carboxyundecanoylamino)butyrylamino]ethoxy}ethoxy)acetylamino]ethoxy}ethoxy)-acetyl][Arg$^{34}$, Lys$^{37}$]GLP-1(9-37)-peptide amide; and N$^{ε26}$-[2-[2-(2-{2-[(S)-4-Carboxy-4-(13-carboxytridecanoylamino)butyrylamino]ethoxy}ethoxy)-acetyl], N$^{ε37}$-[2-[2-(2-{2-[(S)-4-Carboxy-4-(13-carboxytridecanoylamino)butyrylamino]-ethoxy}ethoxy)acetyl][Arg$^{34}$, Lys$^{37}$]GLP-1(9-37)-peptide amide.

In another aspect the glucagon-like peptide to be reacted with the dipeptide according to the invention is a GLP-1 polypeptide which is selected from the group consisting of:
N$^{ε26}$ (17-carboxyheptadecanoyl)-[Arg34]GLP-1-(9-37)-peptide;
N$^{ε26}$-(19-carboxynonadecanoyl)-[Arg34]GLP-1-(9-37)-peptide;
N$^{ε26}$-[2-(2-[2-(2-[2-(2-[4-(17-Carboxyheptadecanoylamino)-4(S)-carboxybutyrylamino]-ethoxy)ethoxy]acetylamino)ethoxy]ethoxy)acetyl][Arg34]GLP-1-(9-37) peptide; and N$^{ε37}$-[2-(2-[2-(2-[2-(2-[4-(21-Carboxyuneicosanoylamino)-4(S)-carboxybutyrylamino]ethoxy)-ethoxy]acetylamino)ethoxy]ethoxy)acetyl][Arg34]GLP-1-(9-37)peptide.

In one aspect a glucagon-like peptide comprising one or more non-proteogenic amino acids is obtained by the method of the invention. In another aspect the glucagon-like peptide comprising one or more non-proteogenic amino acids obtained by the method of the invention is a GLP-1 peptide comprising one or more non-proteogenic amino acids. In a further aspect the GLP-1 peptide comprising one or more non-proteogenic amino acids is a GLP-1 peptide comprising one or more non-proteogenic amino acids and having a side chain mentioned in WO 2006/005667, WO 2005/027978, WO 2011/080103 or WO 2006/097537. In one aspect the GLP-1 peptide comprising one or more non-proteogenic amino acids is Aib$^{8}$, Arg$^{34}$-GLP-1(7-37); Aib$^{8,22}$, Arg$^{34}$-GLP-1(7-37); Aib$^{8}$, Arg$^{34}$, Pro$^{37}$-GLP-1(7-37) or Aib$^{8,22,27,30,35}$, Arg$^{34}$, Pro$^{37}$-GLP-1 (7-37)amide having a side chain mentioned in WO 2006/005667, WO 2005/027978, WO 2011/080103 or WO 2006/097537. In one aspect the GLP-1 peptide comprising one or more non-proteogenic amino acids is a GLP-1 peptide mentioned in WO 2011/080103 in the section on page 84, line 24 bridging on to page 95, line 2, or a GLP-1 analogue mentioned in WO 2006/097537 in the section on page 19, line 25 bridging on to page 22, line 4.

In one aspect the GLP-1 peptide comprising one or more proteogenic amino acids is selected from the group consisting of:
Aib$^{8}$, Arg$^{34}$-GLP-1(7-37);
Aib$^{8,22}$, Arg$^{34}$-GLP-1(7-37);
Arg$^{34}$-GLP-1(7-37);
Aib$^{8}$, Arg$^{34}$, Pro$^{37}$-GLP-1(7-37);
Aib$^{8,22,27,30,35}$, Arg$^{34}$, Pro$^{37}$-GLP-1 (7-37)amide;
N$^{ε26}$-[2-(2-{2-[10-(4-Carboxyphenoxy)decanoylamino]ethoxy} ethoxy)acetyl], N$^{ε37}$-[2-(2-{2-[10-(4-Carboxyphenoxy)decanoylamino]ethoxy}ethoxy)acetyl]-[Aib$^{8}$, Arg$^{34}$, Lys$^{37}$]GLP-1(7-37)peptide;

N$^{ε26}${2-[2-(2-{2-[2-(2-{(S)-4-Carboxy-4-[10-(4-carboxy-phenoxy)decanoylamino]butyrylamino}-ethoxy)ethoxy]acetylamino}ethoxy)ethoxy]acetyl}, N$^{ε37}$-{2-[2-(2-{2-[2-(2-{(S)-4-carboxy-4-[10-(4-carboxyphenoxy)decanoylamino]butyrylamino}ethoxy)ethoxy]acetylamino}-ethoxy)ethoxy]acetyl}-[Aib$^{8}$, Arg$^{34}$, Lys$^{37}$]GLP-1(7-37)-peptide;

N$^{ε26}$-[2-(2-{2-[2-(2-{2-[(S)-Carboxy-4-(15-carboxypentadecanoylamino)butyrylamino]-ethoxy}ethoxy)acetylamino]ethoxy}ethoxy)acetyl], $N^{\varepsilon 37}$-[2-(2-{2-[2-(2-{2-[(S)-4-Carboxy-4-(15-carboxypentadecanoylamino) butyrylamino]ethoxy}ethoxy)acetylamino]ethoxy}-ethoxy)acetyl][Aib$^8$, Arg$^{34}$, Lys$^{37}$]GLP-1(7-37)-peptide amide;

$N^{\varepsilon 26}$-[2-(2-{2-[2-(2-{2-[(S)-4-Carboxy-4-(11-carboxyundecanoylamino)butyrylamino]ethoxy}-ethoxy)acetylamino]ethoxy}ethoxy)acetyl], $N^{\varepsilon 37}$-[2-(2-{2-[2-(2-{2-[(S)-4-Carboxy-4-(11-carboxyundecanoylamino) butyrylamino]ethoxy}ethoxy)acetylamino] ethoxy}ethoxy)-acetyl][Aib$^8$, Arg$^{34}$, Lys$^{37}$]GLP-1(7-37)-peptide amide;

$N^{\varepsilon 26}$-[2-[2-(2-{2-[(S)-4-Carboxy-4-(13-carboxytridecanoylamino)butyrylamino]ethoxy}ethoxy)-acetyl], $N^{\varepsilon 37}$-[2-[2-(2-{2-[(S)-4-Carboxy-4-(13-carboxytridecanoylamino)butyrylamino]-ethoxy}ethoxy)acetyl][Aib$^8$, Arg$^{34}$, Lys$^{37}$]GLP-1(7-37)-peptide amide;

$N^{\varepsilon 26}$ (17-carboxyheptadecanoyl)-[Aib8, Arg34]GLP-1-(7-37)-peptide;

$N^{\varepsilon 26}$-(19-carboxynonadecanoyl)-[Aib8, Arg34]GLP-1-(7-37)-peptide;

$N^{\varepsilon 26}$-[2-(2-[2-(2-[2-(2-[4-(17-Carboxyheptadecanoylamino)-4(S)-carboxybutyrylamino]-ethoxy)ethoxy] acetylamino)ethoxy]ethoxy)acetyl][Aib8, Arg34]GLP-1-(7-37)peptide; and $N^{\varepsilon 26}$-[2-(2-[2-(2-[2-(2-[4-(21-Carboxyuneicosanoylamino)-4(S)-carboxybutyrylamino]ethoxy)-ethoxy]acetylamino) ethoxy]ethoxy)acetyl][Aib8, Arg34]GLP-1-(7-37)peptide.

In one aspect the GLP-1 peptide comprising one or more proteogenic amino acids is selected from the group consisting of:

Aib$^8$, Arg$^{34}$-GLP-1(7-37);
Aib$^{8,22}$, Arg$^{34}$-GLP-1(7-37);
Arg$^{34}$-GLP-1(7-37);
Aib$^8$, Arg$^{34}$, Pro$^{37}$-GLP-1(7-37); and
Aib8,22,27,30,35, Arg$^{34}$, Pro$^{37}$-GLP-1(7-37)amide.

In one aspect the GLP-1 peptide comprising one or more proteogenic amino acids is selected from the group consisting of:

$N^{\varepsilon 26}$-[2-(2-{2-[10-(4-Carboxyphenoxy)decanoylamino] ethoxy} ethoxy)acetyl], $N^{\varepsilon 37}$-[2-(2-{2-[10-(4-Carboxyphenoxy)decanoylamino]ethoxy}ethoxy)acetyl]-[Aib$^8$, Arg$^{34}$, Lys$^{37}$]GLP-1(7-37) peptide;

$N^{\varepsilon 26}${2-[2-(2-{2-[2-(2-{(S)-Carboxy-4-[10-(4-carboxyphenoxy)decanoylamino]butyrylamino}-ethoxy)ethoxy] acetylamino}ethoxy)ethoxy]acetyl}, $N^{\varepsilon 37}$-{2-[2-(2-{2-[2-(2-{(S)-4-carboxy-4-[10-(4-carboxyphenoxy) decanoylamino]butyrylamino}ethoxy)ethoxy] acetylamino}-ethoxy)ethoxy]acetyl}-[Aib$^8$, Arg$^{34}$, Lys$^{37}$] GLP-1(7-37)-peptide;

$N^{\varepsilon 26}$-[2-(2-{2-[2-(2-{2-[(S)-4-Carboxy-4-(15-carboxypentadecanoylamino)butyrylamino]-ethoxy}ethoxy)acetylamino]ethoxy}ethoxy)acetyl], $N^{\varepsilon 37}$-[2-(2-{2-[2-(2-{2-[(S)-4-Carboxy-4-(15-carboxypentadecanoylamino) butyrylamino]ethoxy}ethoxy)acetylamino]ethoxy}-ethoxy)acetyl][Aib$^8$, Arg$^{34}$, Lys$^{37}$]GLP-1(7-37)-peptide amide;

$N^{\varepsilon 26}$-[2-(2-{2-[2-(2-{2-[(S)-4-Carboxy-4-(11-carboxyundecanoylamino)butyrylamino]ethoxy}-ethoxy)acetylamino]ethoxy}ethoxy)acetyl], $N^{\varepsilon 37}$-[2-(2-{2-[2-(2-{2-[(S)-4-Carboxy-4-(11-carboxyundecanoylamino) butyrylamino]ethoxy}ethoxy)acetylamino] ethoxy}ethoxy)-acetyl][Aib$^8$, Arg$^{34}$, Lys$^{37}$]GLP-1(7-37)-peptide amide; and $N^{\varepsilon 26}$-[2-[2-(2-{2-[(S)-4-Carboxy-4-(13-carboxytridecanoylamino)butyrylamino]ethoxy}ethoxy)-acetyl], $N^{\varepsilon 37}$-[2-[2-(2-{2-[(S)-4-Carboxy-4-(13-carboxytridecanoylamino)butyrylamino]-ethoxy}ethoxy)acetyl][Aib$^8$, Arg$^{34}$, Lys$^{37}$]GLP-1(7-37)-peptide amide.

In one aspect the GLP-1 peptide comprising one or more proteogenic amino acids is selected from the group consisting of:

$N^{\varepsilon 26}$ (17-carboxyheptadecanoyl)-[Aib8, Arg34]GLP-1-(7-37)-peptide;

$N^{\varepsilon 26}$-(19-carboxynonadecanoyl)-[Aib8, Arg34]GLP-1-(7-37)-peptide;

$N^{\varepsilon 26}$-[2-(2-[2-(2-[2-(2-[4-(17-Carboxyheptadecanoylamino)-4(S)-carboxybutyrylamino]-ethoxy)ethoxy] acetylamino)ethoxy]ethoxy)acetyl][Aib8, Arg34]GLP-1-(7-37)peptide; and $N^{\varepsilon 26}$-[2-(2-[2-(2-[2-(2-[4-(21-Carboxyuneicosanoylamino)-4(S)-carboxybutyrylamino]ethoxy)-ethoxy]acetylamino) ethoxy]ethoxy)acetyl][Aib8, Arg34]GLP-1-(7-37)peptide.

The production of peptides and proteins is well known in the art. Peptides or proteins may for instance be produced by classical peptide synthesis, e.g. solid phase peptide synthesis using t-Boc or Fmoc chemistry or other well established techniques, see e.g. Greene and Wuts, "Protective Groups in Organic Synthesis", John Wiley & Sons, 1999, "Organic Synthesis on solid Phase", Florencio Zaragoza Dörwald, Wiley-VCH Verlag GmbH, D-69469 Weinheim, 2000, "Novabiochem Catalog", Merck Biosciences 2006/2007 and "Fmoc Solid Phase Peptide Synthesis", Edited by W. C. Chan and P. D. White, Oxford University Press, 2000, ISBN 0-19-963724-5. The peptides or proteins may also be produced by a method which comprises culturing a host cell containing a DNA sequence encoding the peptide or protein and capable of expressing the peptide or protein in a suitable nutrient medium under conditions permitting the expression of the peptide or protein. For peptides or proteins comprising non-natural amino acid residues, the recombinant cell should be modified such that the non-natural amino acids are incorporated into the peptide or protein, for instance by use of tRNA mutants.

The terms "about" or "approximately" as used herein means in reasonable vicinity of the stated numerical value, such as plus or minus 10%, or for pH values plus or minus 0.2 or for temperature plus minus 5 degrees Celsius.

The following is a non-limiting list of embodiments according to the invention:

1. A dipeptide of Chem. 1:

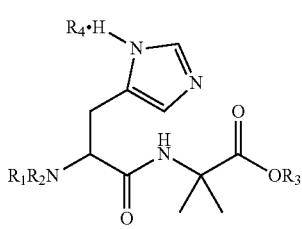

Chem. 1 wherein
R1 is H or an amino protecting group, and R2 is an amino protecting group; or
R1 is a removable alkyl group, and R2 is H or a removable alkyl group; or
R1 and R2 are jointly forming a ring;
R3 is H, or a secondary ammonium cation, a tertiary ammonium cation or a metal cation forming a salt with the carboxylate group; and R4 is absent or an acidic salt.
2. The dipeptide of embodiment 1, wherein the amino protecting group is selected from the group consisting of: Boc, Trt, Bpoc, Fmoc, Nsc, Cbz, Alloc, oNBS, pNBS, dNBS, ivDde and Nps.
3. The dipeptide of embodiment 1 or 2, wherein the removable alkyl group is selected from the group consisting of: Benzyl and tert-Butyl.
4. The dipeptide of any one of embodiments 1-3, wherein, when R1 and R2 are jointly forming a ring, the jointly formed ring is selected from the group consisting of: Phatalimide and 1,3,5-dioxazine.
5. The dipeptide of any one of embodiments 1-4, wherein
R1 is H or an amino protecting group selected from the group consisting of: Boc, Trt, Bpoc, Fmoc, Nsc, Cbz, Alloc, oNBS, pNBS, dNBS, ivDde and Nps, and R2 is an amino protecting group selected from the group consisting of: Boc, Trt, Bpoc, Fmoc, Nsc, Cbz, Alloc, oNBS, pNBS, dNBS, ivDde and Nps; or
R1 is a removable alkyl group selected from the group consisting of: Benzyl and tert-Butyl, and R2 is H or a removable alkyl group selected from the group consisting of: Benzyl and tert-Butyl; or
R1 and R2 are jointly forming a ring selected from the group consisting of: Phatalimide and 1,3,5-dioxazine;
R3 is H, or a secondary ammonium cation, a tertiary ammonium cation, an alkali metal cation or an alkaline earth metal cation forming a salt with the carboxylate group; and
R4 is absent or an acidic salt selected from the group consisting of: A salt of TFA, a salt of HCl, a salt of HBr and a salt of hydrogensulfate.
6. The dipeptide of any one of embodiments 1-5, wherein
R1 is H or an amino protecting group selected from the group consisting of: Boc, Trt, Bpoc, Fmoc, Nsc, Cbz, Alloc, oNBS, pNBS, dNBS, ivDde and Nps, and
R2 is an amino protecting group selected from the group consisting of: Boc, Trt, Bpoc, Fmoc, Nsc, Cbz, Alloc, oNBS, pNBS, dNBS, ivDde and Nps.
7. The dipeptide of any one of embodiments 1-5, wherein R1 is H and R2 is an amino protecting group selected from the group consisting of: Boc, Trt, Bpoc, Fmoc, Nsc, Cbz, Alloc, oNBS, pNBS, dNBS, ivDde and Nps.
8. The dipeptide of any one of embodiments 1-5, wherein R1 is H and R2 is Fmoc.
9. The dipeptide of any one of embodiments 1-5, wherein R1 is an amino protecting group selected from the group consisting of: Boc, Trt, Bpoc, Fmoc, Nsc, Cbz, Alloc, oNBS, pNBS, dNBS, ivDde and Nps, and
R2 is an amino protecting group selected from the group consisting of: Boc, Trt, Bpoc, Fmoc, Nsc, Cbz, Alloc, oNBS, pNBS, dNBS, ivDde and Nps.
10. The dipeptide of any one of embodiments 1-5, wherein R1 is a removable alkyl group selected from the group consisting of: Benzyl and tert-Butyl, and
R2 is H or a removable alkyl group selected from the group consisting of: Benzyl and tert-Butyl.
11. The dipeptide of any one of embodiments 1-5, wherein R1 is a removable alkyl group selected from the group consisting of: Benzyl and tert-Butyl, and
R2 is H.
12. The dipeptide of any one of embodiments 1-5, wherein R1 is a removable alkyl group selected from the group consisting of: Benzyl and tert-Butyl, and
R2 is a removable alkyl group selected from the group consisting of: Benzyl and tert-Butyl.

13. The dipeptide of any one of embodiments 1-12, wherein R3 is H.
14. The dipeptide of any one of embodiments 1-12, wherein R3 is a secondary ammonium cation forming a salt with the carboxylate group.
15. The dipeptide of any one of embodiments 1-12, wherein R3 is a tertiary ammonium cation forming a salt with the carboxylate group.
16. The dipeptide of any one of embodiments 1-12, wherein R3 is an alkali metal cation forming a salt with the carboxylate group.
17. The dipeptide of any one of embodiments 1-12, wherein R3 is an alkaline earth metal cation forming a salt with the carboxylate group.
18. The dipeptide of any one of embodiments 1-17, wherein R4 is absent.
19. The dipeptide of any one of embodiments 1-17, wherein R4 is an acidic salt selected from the group consisting of: A salt of TFA, a salt of HCl, a salt of HBr and a salt of hydrogensulfate.
20. The dipeptide according to any one of embodiments 1-19, wherein
R1 is H;
R2 is Fmoc;
R3 is H; and
R4 is absent or an acidic salt such as TFA, HCl, HBr or HOAc.
21. The dipeptide according to any one of embodiments 1-3, which is
Fmoc-His-Aib-OH of Chem. 2

Chem. 2

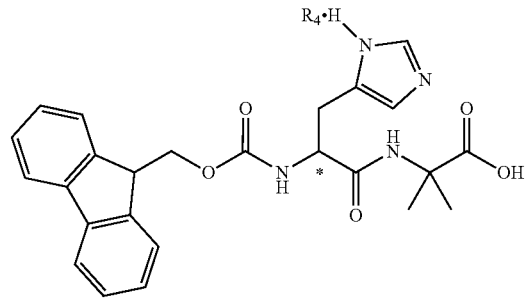

wherein His is histidine, Aib is the artificial amino acid 2-aminoisobutyric acid, Fmoc is the protection group 9-fluorenylmethyloxycarbonyl and R4 is absent or an acidic salt such as TFA, HCl, HBr or HOAc.
22. The dipeptide according to any one of embodiments 1-3, which is the TFA salt of Fmoc-His-Aib-OH:
Fmoc-His-Aib-OH, TFA
wherein His is histidine, Aib is the artificial amino acid 2-aminoisobutyric acid, Fmoc is the protection group 9-fluorenylmethyloxycarbonyl and TFA is trifluoroacetic acid.
23. The dipeptide according to any one of embodiments 1-22, which is activated by an activating agent such as a phosphonium based coupling reagent such as (benzotriazol-1-yloxy)tripyrrolidinophosphonium hexafluorophosphate (PyBOP).
24. A method for producing a dipeptide according to any one of embodiments 1-23.
25. A method for obtaining a polypeptide or protein comprising one or more non-proteogenic amino acids, wherein the method comprises a step of reacting the dipeptide according to any one of embodiments 1-23 with a polypeptide or protein.

26. A method for obtaining a polypeptide or protein according to embodiment 25, wherein said dipeptide is reacted with a polypeptide or protein in an aqueous media.

27. A method for obtaining a polypeptide or protein according to embodiment 25, comprising the step of mixing the dipeptide and the polypeptide or protein in an aqueous media.

28. A method for obtaining a polypeptide or protein according to any one of embodiments 25-27, wherein R1 and/or R2 of said dipeptide is removed after completion of the reaction with a polypeptide or protein.

29. A method for obtaining a polypeptide or protein according to any one of embodiments 25-28, wherein R1 and/or R2 of said dipeptide is removed in a deprotection step under basic conditions.

30. A method for obtaining a polypeptide or protein according to any one of embodiments 25-29, wherein R1 and/or R2 of said dipeptide is removed in a deprotection step wherein a piperidine is added to the reaction medium.

31. A method for obtaining a polypeptide or protein according to any one of embodiments 25-30, wherein R1 and/or R2 of said dipeptide is removed in situ in one chemical step after completion of the acylation reaction with a polypeptide or protein.

32. A method for obtaining a polypeptide or protein according to any one of embodiments 25-31 wherein the polypeptide or protein is N-terminal Fmoc protected, comprising a step wherein the N-terminal Fmoc protected polypeptide or protein is deprotected in situ.

33. A method for obtaining a polypeptide or protein according to any one of embodiments 25-32, wherein the method comprises the steps:
   1. activating a dipeptide of Chem. 1 or Chem 2. with a phosphonium based coupling reagent.
   2. reacting said activated dipeptide with a polypeptide or protein
   3. removing the protecting group(s) in situ
   whereby the final polypeptide or protein is obtained.

34. A method for obtaining a polypeptide or protein according to embodiment 33, wherein in step 2 said activated dipeptide is reacted with a polypeptide or protein in an aqueous media.

35. A method for obtaining a polypeptide or protein according to any one of embodiments 26-34, wherein said aqueous media comprises one or more water soluble organic solvents selected from the group consisting of: DMF, NMP, DMAC, DMSO, acetonitrile, dioxane, butoxy-2-ethanol, a water soluble acetal and a water soluble alcohol.

36. A method for obtaining a polypeptide or protein according to embodiment 35, wherein said one or more water soluble organic solvents is NMP.

37. A method for obtaining a polypeptide or protein according to any one of embodiments 26-36, wherein the aqueous media in which said activated dipeptide is reacted with a polypeptide or protein comprises 10-100% water.

38. A method for obtaining a polypeptide or protein according to any one of embodiments 26-36, wherein the aqueous media in which said activated dipeptide is reacted with a polypeptide or protein comprises about 40% water.

39. A method for obtaining a polypeptide or protein according to any one of embodiments 26-38, wherein pH of the aqueous media is between pH 7 and pH 14.

40. A method for obtaining a polypeptide or protein according to any one of embodiments 26-38, wherein pH of the aqueous media is between pH 8.7 and pH 9.4.

41. A method for obtaining a polypeptide or protein according to any one of embodiments 26-38, wherein pH of the aqueous media is about pH 9.1.

42. A method for obtaining a polypeptide or protein according to any one of embodiments 26-38, wherein pH of the aqueous media is about pH 9.3.

43. A method for obtaining a polypeptide or protein according to any one of embodiments 26-38, wherein the aqueous media comprises a buffer.

44. A method for obtaining a polypeptide or protein according to any one of embodiments 25-38, wherein the polypeptide or protein comprising one or more non-proteogenic amino acids is obtained in solution.

45. A method for obtaining a polypeptide or protein according to any one of embodiments 1-23, wherein the polypeptide or protein reacted with said dipeptide is immobilised on a solid phase.

46. The method for obtaining a polypeptide or protein according to any one of embodiments 1-23, wherein said dipeptide is reacted with the α-N-terminal of the polypeptide or protein.

47. The method for obtaining a polypeptide or protein according to any one of embodiments 1-23, wherein the polypeptide or protein to be reacted with said dipeptide is a GLP-1 peptide.

EXAMPLES

List of Abbreviations

ADO: 8-Amino-3,6-dioxaoctanoic acid
Aib: 2-aminoisobutyric acid
Alloc: Allyloxycarbonyl
Boc: tert-Butoxycarbonyl
Bpoc: 2-(p-biphenylyl)-2-propyloxycarbonyl
Cbz: Benzyloxycarbonyl
DCM: Dichloromethane
DIC: N,N'-Diisopropylcarbodiimide
DIPEA: N,N-Diisopropylethylamine
DME: Dimethyl ether
dNBS: 2,4-Dinitrobenzenesulfonyl
EtOH: Ethanol
Fmoc: 9-fluorenylmethyloxycarbonyl
HBr: Hydrobromic acid
HCl: Hydrochloric acid
His: Histidine
HOAc: Acetic acid
HOBt: Hydroxybenzotriazole
ivDde: 1-(4,4-Dimethyl-2,6-dioxocyclo-Hexylidene)-3-methylbutyl
Lys: Lysine
MeCN: Acetonitrile
Mtt: 4-Methyltrityl
NMP: N-Methyl-2-pyrrolidone
Nps: o- or p-Nitrophenylsulfenyl
Nsc: 2-(4-Nitrophenyl)sulfonylethoxycarbonyl
oNBS: o-Nitrobenzenesulfonyl
OtBu: tert-Butoxy
pNBS: p-Nitrobenzenesulfonyl
PyBOP: (Benzotriazol-1-yloxy)tripyrrolidinophosphonium hexafluorophosphate
TBME: tert-Butyl methyl ether
TBTU: O-(Benzotriazol-1-yl)-N,N,N',N'-tetramethyluronium tetrafluoroborate TEA: Trimethylamine
TFA: Trifluoroacetic acid
TIPS: Triisopropylsilane
Trt: Triphenylmethyl

Example 1

2-[(S)-2-(9H-Fluoren-9-ylmethoxycarbonylamino)-3-(1H-imidazol-4-yl)-propanoylamino]-2-methyl-propanoic Acid Trifluoracatate (Alternative Name: Fmoc-His-Aib-OH, TFA)

Chem. 3

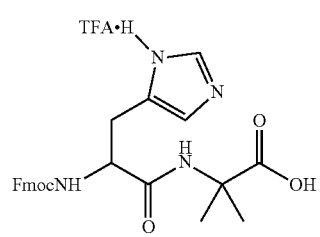

Fmoc-His(Trt)-Aib-OH (1 moleq., starting material) was suspended in DCM (1.5 mL/g) and TIPS (1.7 moleq.) was added. Cooled (0-10° C.) TFA (3 mL/g) was added and the mixture was stirred at ambient temperature until the reaction was completed (High-performance liquid chromatography (HPLC) conversion). DME (1 mL/g starting material) and TBME (11 mL/g starting material) was added leading to an increase in temperature. The temperature was slowly allowed to return to room temperature (rt) resulting in precipitation of a white solid. The mixture was stirred for an additional 3 hr and filtered. The precipitate was washed twice with TBME (3 mL/g starting material) and dried overnight in vacuo affording the de-tritylated dipeptide as TFA-salt in 90% yield.
Stability studies at freeze (<−15° C.±5° C.), fridge (5° C.±3° C.), and room temperature (20° C.±3° C.) shows more than 24 month stability.

NMR data:

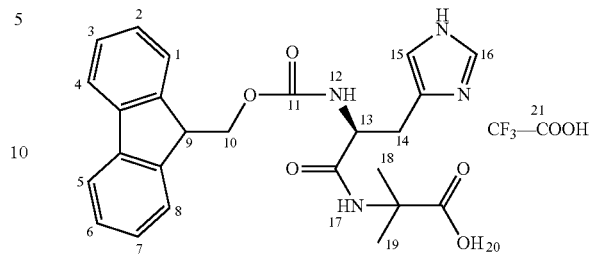

| $^1$H | Chemical Shift δ (ppm) | Inte-gral | Coupling Pattern | Coupling Constants $^nJ_{HH}$ (Hz) |
|---|---|---|---|---|
| H18 | 1.34 | 3 H | singlet | ND |
| H19 | 1.38 | 3 H | singlet | ND |
| H14 | 2.93 | 1 H | Double dublet | $^1J_{HH}$ = 14, $^3J_{HH}$ = 9 |
| H14' | 3.08 | 1 H | Double dublet | $^2J_{HH}$ = 14, $^3J_{HH}$ = 5 |
| H9 | 4.20 | 1 H | Multiplet | ND |
| H10, H10' | 4.25 | 2 H | Multiplet | ND |
| H13 | 4.37 | 1 H | multiplet | ND |
| H2, H7 | 7.33 | 2 H | Triplet | $^3J_{HH}$ = 7 |

NMR data:

| $^1$H | Chemical Shift δ (ppm) | Inte-gral | Coupling Pattern | Coupling Constants $^nJ_{HH}$ (Hz) |
|---|---|---|---|---|
| H15 | 7.33 | 1 H | Singlet | ND |
| H3, H6 | 7.42 | 2 H | Triplet | $^3J_{HH}$ = 7 |
| H1, H8 | 7.68 | 2 H | Dublet | $^3J_{HH}$ = 7 |
| H12 | 7.71 | 1 H | Dublet | $^3J_{HH}$ = 8.5 |
| H4, H5 | 7.90 | 2 H | dublet | $^3J_{HH}$ = 7 |
| H17 | 8.17 | 1 H | singlet | ND |
| H16 | 8.97 | 1 H | singlet | ND |
| H20 | 12.5 | 1 H | br.singlet | ND |

Example 2

[(S)-(22,40-dicarboxy-10,19,24-trioxo-3,6,12,15-tetraoxa-9,18,23-triazatetracontan-1-oyl)][Aib$^8$, Arg$^{34}$]GLP-1-(7-37) peptide (Alternative Name: N$^{\varepsilon 26}$ [2-(2-{2-[2-(2-{2-[(S)-4-Carboxy-4-(17-carboxy-heptadecanoylamino)-butyrylamino]ethoxy}-ethoxy)-acetylamino]-ethoxy}-ethoxy)-acetyl][Aib$^8$, Arg$^{34}$]GLP-1-(7-37) peptide)

Step 1
In Situ Activation of dipeptide Fmoc-His-Aib-OH, TFA (Mixture I):
To a mixture of Fmoc-His-Aib-OH, TFA (4 moleq.) and HOBt*H$_2$O (4 moleq.) was added NMP (4.7 mL/g dipeptide) at ambient temperature. To the stirred solution TEA was added until pH 8, while the temperature of the solution was kept at ambient temperature using an ice-bath. A solution of PyBOP (3.9 moleq.) in NMP (2.4 mL/g dipeptide) was added to the solution containing the dipeptide at ambient temperature. The pH of the reaction mixture was adjusted to pH 8 by use of TEA. The mixture was stirred at ambient temperature for 20 min. prior to the addition to mixture II.
Preparation of Peptide
(N$^{\varepsilon 26}$ [(S)-(22,40-dicarboxy-10,19,24-trioxo-3,6,12,15-tetraoxa-9,18,23-triazatetracontan-1-oyl)] [Arg$^{34}$]GLP-1-(9-37) peptide (alternative name: N$^{\varepsilon}26$ [2-(2-{2-[2-(2-{2-[(S)-4-Carboxy-4-(17-carboxy-heptadecanoylamino)-butyrylamino]-ethoxy}-ethoxy)-acetylamino]ethoxy}-ethoxy)-acetyl][Arg$^{34}$]GLP-1-(9-37) peptide for acylation (Mixture II): N$^{\varepsilon 26}$ [(S)-(22,40-dicarboxy-10,19,24-trioxo-3,6,12,15-tetraoxa-9,18,23-triazatetracontan-1-oyl)] [Arg$^{34}$] GLP-1-(9-37) was suspended in 40 w/w % H$_2$O in NMP (37 g peptide/L solvent mixture). To the cooled suspension was added TEA until pH 9.3.
Step 2:
Acylation of peptide N$^{\varepsilon 26}$ [(S)-(22,40-dicarboxy-10,19,24-trioxo-3,6,12,15-tetraoxa-9,18,23-triazatetracontan-1-oyl)] [Arg$^{34}$]GLP-1-(9-37) peptide (Mixture III):

Mixture I was added dropwise to mixture II at ambient temperature. After addition the pH was readjusted to pH 9.3 (pH-meter) by TEA. The mixture was stirred until optimal conversion (measured by HPLC).
Step 3:
Removal of Protecting Group (Fmoc)
To the mixture III was added piperidine (20 moleq./dipeptide) and the mixture was stirred for 40 min at rt.
Orbitrap m/z 1028.7 (4+) 1371.4 (3+)

Example 3

Preparation of $N^\epsilon 26,N^\epsilon 37$-bis[(S)-(22-carboxy-33-(4-carboxyphenoxy)-10,19,24-trioxo-3,6,12,15-tetraoxa-9,18,23-triazatritriacontan-1-oyl)][Aib8, Arg34, Lys37]GLP-1-(7-37) peptide (Alternative Name: $N^{\epsilon 26}$-[2-[2-[2-[[2-[2-[2[[(4S)-4-carboxy-4-[10-(4-carboxyphenoxy)decanoylamino]butanoyl]amino]ethoxy]ethoxy]acetyl]amino]ethoxy]ethoxy]acetyl]-, $N^{\epsilon 37}$-[2-[2-[2-[[2-[2-[2-[[(4S)-4-carboxyl-4-[10-(4-carboxyphenoxy)decanoylamino]butanoyl]amino]ethoxy]ethoxy]acetyl]amino]ethoxy]ethoxy]acetyl]-[Aib$^8$, Arg$^{34}$, Lys$^{37}$]-GLP-1-(7-37)-peptide)

Step 1: Sidechain Acylation
[Arg$^{34}$, Lys$^{37}$]-GLP-1-(9-37)-peptide as an isoprecipitated pellet (15 g, peptide content of approximately 13% w/w, purity of ~93%) was suspended in water (50 mL) and NaOH (aq) (1 M; 1150 µL) was added to dissolve the peptide. The resulting solution (57 mL) was transferred to a 150 mL reaction chamber in a titrater setup. The pH of the solution was measured to 10.6. The pH was by the titrator adjusted to 11.3 with dilute NaOH (aq) (0.5 M, 0.67 mL) and the volume adjusted with water to 60 mL giving a final peptide concentration of approximately 33 mg/mL. Assaying the solution to a standard curve of [Arg$^{34}$, Lys$^{37}$]-GLP-1-(9-37)-peptide gave a corrected peptide content of 1.71 g. Using 1.71 g peptide gave a corrected concentration of the solution of 28.5 mg/mL. Activated sidechain 2,5-dioxopyrrolidin-1-yloxy (S)-(22-carboxy-33-(4-carboxyphenoxy)-10,19,24-trioxo-3,6,12,15-tetraoxa-9,18,23-triazatritriacontanate (alternative name: (4-[9-((S)-1-Carboxy-3-{2-[2-({2-[2-(2-hydroxy-5-oxo-pyrrolidin-1-yloxycarbonylmethoxy)-ethoxy]-ethylcarbamoyl}-methoxy)-ethoxy] ethylcarbamoyl}-propylcarbamoyl)-nonyloxy]-benzoic acid) as 83% active ester, 1.73 g 3.3 eq) was dissolved in NMP (4.8 mL) giving 5.20 mL of solution (0.63 eq/mL). The NMP solution of the sidechain was added slowly from a syringe pump at a constant speed keeping pH constant at 11.3 by titrator controlled addition of aq. NaOH (aq) (0.5 M). 3.90 mL (2.4 eq) of sidechain was added over 1 h and 10 minutes ~2 eq/h). Ultra Performance Liquid Chromatography (UPLC) analysis showed the acylation to be almost complete and addition was continued to a total of 2.8 eq of sidechain (4.43 mL). During addition a total of (16.71 mL; 8.4 mmol) 0.5 N NaOH (aq) was added by the titrator.
Step 2: Isoprecipitation
The reaction mixture was transferred with water to 4×50 mL centrifuge vials (22 mL in each) and pH in each was adjusted to 4.8 by addition of conc. acetic acid to give a white precipitate. EtOH (2.2 mL to a total of app. 10% v/v) was added. The precipitate was centrifuged and used without further purification in the next step.
Step 3: Ligation of Dipeptide
The isoprecipitate was suspended in NMP (48 mL; 50 mg peptide/mL) and DIPEA (656 µL) was added. pH of the resulting solution was measured to pH=9.6 in a sample of 100 µL of the mixture diluted with 900 µL water.
The water content of the slurry was measured to 1.4% by Karl Fischer titration. Water (9.12 mL) was added to give a water content of app. 20%.
Fmoc-His-Aib-OH, TFA; 1058 mg, 3.5 eq) was activated with HOBt (248 mg; 3.5 eq), PyBOP (907 mg, 3.325 eq) and triethylamine (545 µL) in NMP for 15 minutes. pH was 4-5 measured by a wet pH stick. The mixture was added to the peptide solution and pH was adjusted with triethylamine to pH 9.3 (by measuring a sample of the reaction mixture (100 µL) added to water (900 µL). After 1 h UPLC showed almost complete conversion to the desired product.
Step 4: Fmoc Deprotection
To the reaction mixture from the ligation step was added piperidine (3.35 mL, (5% v/v)) and the mixture was stirred for 25 minutes after which UPLC analysis showed complete conversion to the product. Water was added to give a 1:1 NMP-water solution and the pH was adjusted to 8.5 with acetic acid and the product purified by standard chromatography.
Analysis:
RP-UPLC: BEH C18, 150*1 mm@45° C. and 0.1 ml/min; gradient from 30 to 60% 0.04% TFA in MeCN (B eluent) in 30 min then up to 90% B, total run time 38 min. UV@215 nm, 5 Hz Synapt High Definition Mass Spectrometry (HDMS): positive ES-MS mode from m/z 200-2500 (1 Hz). V(cap): 3 kV; V(cone): 28V; Desolvation gas 250° C.@750 l/h; cone gas 50 l/h@110° C.
Rt=15.18 min
Exact mass: 4885, 4477 Da; Found: M/4: 1222.35; M/3: 1629.45

Example 4

Preparation of $N^{\epsilon 26}$[(S)-(22-carboxy-33-(4-carboxyphenoxy)-10,19,24-trioxo-3,6,12,15-tetraoxa-9,18,23-triazatritriacontan-1-oyl)][Aib$^8$, Arg$^{34}$, Lys$^{37}$] GLP-1-(7-37) peptide (Alternative Name: $N^{\epsilon 26}$-[2-[2-[2-[[2-[2-[2-[[(4S)-4-carboxy-4-[10-(4-carboxyphenoxy)decanoylamino]butanoyl]amino] ethoxy]ethoxy]acetyl]amino]ethoxy]ethoxy]acetyl]-[Aib$^8$, Arg$^{34}$, Lys$^{37}$]-GLP-1-(7-37)-peptide)

The peptide was synthesised using solid phase peptide synthesis:
To the 1.04 g resin Fmoc-Lys(Boc)-Wang-LL (eq. 0.24 mmol/g) was added in a stepwise manner 4 moleq. Standard Fmoc/OtBu protocol protected amino acids or Ser-Ser pseudoproline or Fmoc-L-Lys(Mtt)-OH. The activation amino acid (4 moleq.) in cartridge was reacted for 7 minutes with 4 moleq DIC and 4 moleq. HOBt in NMP. The resulting peptide was transferred to a reaction vessel with resin and reacted for 30 min. DIPEA (4 moleq.) was added and the reaction was continued for 30 min. The resin was flowwashed with NMP and subsequently deprotected using 20% Piperidine (10 ml, 20 min). The resin was again flowwashed with NMP.
MTT Deprotection:
The resin was washed in DCM. 1,1,1,3,3,3-hexafluoro-2-propanol (10 ml for 10 min) was added and the resin was drained. The deprotection procedure was repeated overall four times. The resin was washed with DCM, followed by NMP.
To a mixture of (S)-22-(tert-butoxycarbonyl)-33-(4-(tert-butoxycarbonyl)phenoxy)-10,19,24-trioxo-3,6,12,15-tetraoxa-9,18,23-triazatritriacontan-1-oic acid, HOBt (4 moleq.) and DIPEA (4 moleq.) in NMP (10 ml) was added, and TBTU (3.8 moleq.) was added as a solid, and the mixture was shaken for 15 min. before added to the resin. After 2 hr. the resin was drained and flowwashed with NMP and DCM.

The peptidyl resin was swelled in NMP (10 mL) for 10 min at ambient temperature. The vessel was drained. 20 vol % piperidine in NMP (20 mL) was added to the resin. The mixture was swelled for 20 min at ambient temp. The dipeptide Fmoc-L-His-Aib-OH, TFA (580 mg) and HOBt.H₂O (153 mg) were placed in a 20 mL vial. NMP (4 mL) was added. To the mixture was added TEA (650 µL) until pH 8 (pH-stick). To the reaction mixture was added a solution of PyBOP (500 mg) in NMP (4 mL). To the reaction mixture was again added TEA (200 µL) until pH 8 (pH-stick). The mixture was stirred for 35 min at ambient temp. The vessel was drained. 20 vol % piperidine in NMP (20 mL) was again added to the resin (double deprotection). The mixture was swelled for 20 min at ambient temp and the resin was drained. The resin was flow washed with NMP (50 mL), DCM (50 mL) and 3 times NMP (50 mL). Finally the resin was flowwashed with DCM and drained. The peptide was cleaved from the resin by a mixture of TFA, H₂O and TIPS (95%, 2.5%, 2.5%) for 3 hr. The resulting cleaved peptide was precipitated in diethylether and isolated by filtration.

TOF MS ES+: m/z, found m/4 (1045.54), calculated m/4 (1045.5)

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of preparing a final polypeptide or protein, comprising:
   (a) providing a polypeptide or protein containing one or more non-proteogenic amino acids;
   (b) providing a dipeptide having a free unprotected imidazolyl moiety, wherein the dipeptide is

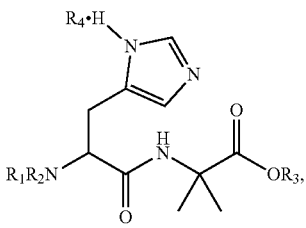

and wherein
R1 and R2 are selected from the group consisting of
(i) R1 is H or an amino protecting group and R2 is an amino protecting group,
(ii) R1 is a removable alkyl group and R2 is H or a removable alkyl group, and
(iii) R1 and R2 jointly form a ring;
R3 is selected from the group consisting of H, a secondary ammonium cation, a tertiary ammonium cation, and a metal cation forming a salt with the carboxylate group; and
R4 is an acid;

(c) activating the dipeptide by contacting the dipeptide with a phosphonium-based coupling reagent; and
(d) reacting the activated dipeptide with the α-N-terminal of the polypeptide or protein to obtain the final polypeptide or protein.

2. The method according to claim 1, wherein the amino protecting group is selected from the group consisting of: tert-Butoxycarbonyl (Boc), Triphenylmethyl (Trt), 2-(p-biphenylyl)-2-propyloxycarbonyl (Bpoc), 9-fluorenylmethyloxycarbonyl (Fmoc), 2-(4-Nitrophenyl)sulfonylethoxycarbonyl (Nsc), Benzyloxycarbonyl (Cbz), Allyloxycarbonyl (Alloc), o-Nitrobenzenesulfonyl (oNBS), p-Nitrobenzenesulfonyl (pNBS), 2,4-Dinitrobenzenesulfonyl (dNBS), 1-(4,4-Dimethyl-2,6-dioxocyclo-Hexylidene)-3-methylbutyl (ivDde) and o- or p-Nitrophenylsulfenyl (Nps).

3. The method according to claim 1, wherein the removable alkyl group is selected from the group consisting of Benzyl and tert-Butyl.

4. The method according to claim 1, wherein R1 and R2 jointly form a ring is selected from the group consisting of Phatalimide and 1,3,5-dioxazine.

5. The method according to claim 1, wherein
(i) R1 is H or an amino protecting group selected from the group consisting of Boc, Trt, Bpoc, Fmoc, Nsc, Cbz, Alloc, oNBS, pNBS, dNBS, ivDde and Nps, and R2 is an amino protecting group selected from the group consisting of Boc, Trt, Bpoc, Fmoc, Nsc, Cbz, Alloc, oNBS, pNBS, dNBS, ivDde, and Nps; or
R1 is a removable alkyl group selected from the group consisting of Benzyl and tert-Butyl, and R2 is H or a removable alkyl group selected from the group consisting of Benzyl and tert-Butyl; or
R1 and R2 jointly form a ring selected from the group consisting of Phatalimide and 1,3,5-dioxazine;
(ii) R3 is selected from the group consisting of H, a secondary ammonium cation, a tertiary ammonium cation, an alkali metal cation, and an alkaline earth metal cation forming a salt with the carboxylate group; and
(iii) R4 is selected from the group consisting of TFA, HCl, HBr, and hydrogensulfate.

6. The method according to claim 1, wherein R4 is selected from the group consisting of TFA, HCl, HBr, and hydrogensulfate.

7. The method according to claim 1, wherein the dipeptide is

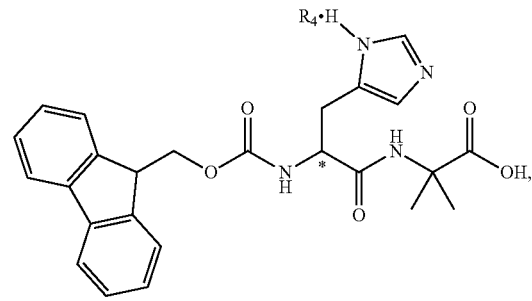

wherein * indicates the chiral center of the dipeptide and R4 is selected from the group consisting of TFA, HCl, HBr, hydrogensulfate, and HOAc.

8. The method according to claim 1, wherein the dipeptide is Fmoc-His-Aib-OH, TFA, wherein His is histidine, Aib is the artificial amino acid 2-aminoisobutyric acid, Fmoc is the protection group 9-fluorenylmethyloxycarbonyl, and TFA is trifluoroacetic acid.

9. The method according to claim 1, wherein the dipeptide is attached to the polypeptide or protein of (a) at a histidine residue.

10. The method according to claim 9, wherein the histidine residue is a L-histidine.

11. The method according to claim 1, wherein the phosphonium-based coupling reagent is (benzotriazol-1-yloxy) tripyrrolidinophosphonium hexafluorophosphate (PyBOP).

12. The method according to claim 1, wherein the activating further comprises dissolving the dipeptide in an aprotic organic solvent before the reacting.

13. The method according to claim 12, wherein the aprotic organic solvent is selected from the group consisting of DMF, NMP, DMAC, DMSO, acetonitrile, dioxane, and mixtures thereof.

14. The method according to claim 1, wherein one or both of R1 and R2 are removed in a deprotection step under basic conditions.

15. The method according to claim 1, wherein the reacting is performed in aqueous media at a pH between 8.7 and 9.4.

16. The method according to claim 1, wherein the final GLP-1 polypeptide is $N^{E26}$-[2-(2-[2-(2[2-(2-[4-(17-Carboxyheptadecanoylamino)-4(S)-carboxybutyrylamino]ethoxy)ethoxy]-acetylamino)ethoxy]ethoxy)acetyl][Aib 8,Arg34]GLP-1-(7-37)peptide.

17. The method according to claim 5, wherein the final GLP-1 polypeptide is $N^{E26}$-[2-(2-[2-(2-[2-(2-[4-(17-Carboxyheptadecanoylamino)-4(S)-carboxybutyrylamino]ethoxy)ethoxy]-acetylamino)ethoxy]ethoxy)acetyl][Aib 8,Arg34]GLP-1-(7-37)peptide.

18. The method according to claim 7, wherein the final GLP-1 polypeptide is $N^{E26}$-[2-(2-[2-(2-[2-(2-[4-(17-Carboxyheptadecanoylamino)-4(S)-carboxybutyrylamino]ethoxy)ethoxy]- acetylamino)ethoxy] ethoxy)acetyl] [Aib8, Arg34]GLP-1-(7-37)peptide.

* * * * *